United States Patent [19]

Jessel, Jr.

[11] Patent Number: Plant 7,747

[45] Date of Patent: Dec. 10, 1991

[54] CARNATION PLANT NAMED CFPC CONTRAST

[75] Inventor: Walter H. Jessel, Jr., Salinas, Calif.

[73] Assignee: California Florida Plant Co., L.P., Salinas, Calif.

[21] Appl. No.: 553,713

[22] Filed: Jul. 16, 1990

[51] Int. Cl.[5] ..... A01H 5/00

[52] U.S. Cl. ..... Plt./70

[58] Field of Search ..... Plt./70, 71, 72, 73

[56] References Cited

U.S. PATENT DOCUMENTS

P.P. 5,204 3/1984 Klemm ..... Plt. 70

*Primary Examiner*—Howard J. Locker

*Attorney, Agent, or Firm*—Christie, Parker & Hale

[57] ABSTRACT

A new and unusual carnation of pink flush coloration.

1 Drawing Sheet

BACKGROUND OF THE INVENTION

Carnation varieties producing flowers of many different colors are well known. However, it is desirable to provide a new standard variety of carnation producing flowers having pink flush coloration.

SUMMARY OF THE INVENTION

The present invention relates to a new and distinct variety of coloration plant which was originated by me in a controlled breeding program by my crossing as seed parent, the variety known as 'Yasmina Barsemi' (U.S. Plant Pat. No. 3,533) and as pollen parent, a numbered but unnamed and unpatented seedling of my creation. The varietal denomination of this new carnation is 'CFPC Contrast'.

Among the novel characteristics possessed by the new variety which distinguishes it from its parents and all other varieties of which I am aware is the unusual pink flush or pink "frosted" flower coloring in a standard. Flowers of the new variety have early uniform response, excellent vase-life and are resistant to botrytis.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development (tight bud, partially opened bud and full bloom), depicted in color as nearly true as it is reasonably possible to make the same in a color illustration of this character.

DESCRIPTION OF THE NEW VARIETY

The new variety, CFPC Contrast, produces flowers which are resistant to botrytis and are long lasting after cutting. It has been determined that its vase-life averages 21-days. The new variety also has a strong calyx with very little splitting. Therefore, taping or banding is not necessary. CFPC Contrast also exhibits early uniform response which, together with its attractive pink flush coloring and the other characteristics heretofore and hereinafter described, make it especially suitable for commercial cut flower production.

The following is a detailed description of my new variety, with color terminology in accordance with The Royal Horticultural Society Color Chart (RHSCC). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Contrast.

Classification:

*Botanical.*—*Dianthus caryophyllus.*

*Commercial.*—Carnation, standard disbud type.

Parentage:

*Female parent.*—'Yasmina Barsemi'.

*Male parent.*—Unnamed seedling (No. 0095).

Plant:

*Height.*—About 44 inches.

*Growing habit.*—Herbaceous, semi-upright.

*Blooming habit.*—Terminal as a disbud.

*Blooming season.*—Continuous.

*Rooting time.*—17-20 days.

*Mutation prone.*—No.

*Disease resistance.*—Unknown.

*Temperature tolerance.*—Typical for carnation.

Foliage:

*Color.*—Upper side: Near to 137A. Lower side: Near to 137A.

*Size.*—About 6¾ inches long, about ½-inch wide at base of plant.

*Quantity.*—Numerous.

*Shape.*—Elongated, curled.

*Texture.*—Smooth.

*Ribs.*—Prominent central keel.

*Arrangement.*—Bi-lateral along stem.

Bloom:

*Form.*—Circular, high.

*Shape.*—Crown coarsely serrated at petal edge.

*Size.*—Diameter average: About 3¼ inches. Depth average: About 2¼ inches.

*Borne.*—Terminal as disbudded.

*Color.*—General tonality: Dark pink with white border. Upper side: Near to from 53C to red purple 66D (faded). Lower side: Near to from 55B to red purple 68C. Center: Near to 53C. Outer petals: Whiter than 155D.

*Permanence.*—Yes.

*Keeping habit.*—Excellent.

*Fragrance.*—Slight.

Petals:

*Number.*—About 38–40.

*Outer petals.*—Length: About 2¼ inches. Width: About 1⅝ inches.

*Texture.*—Smooth.

*Form.*—Fan shaped.

Reproduction organs: Not visible in this variety.

I claim:

1. A new and distinct variety of carnation plant, substantially as shown and described, characterized particularly by flowers of attractive pink flush coloration.

* * * * *

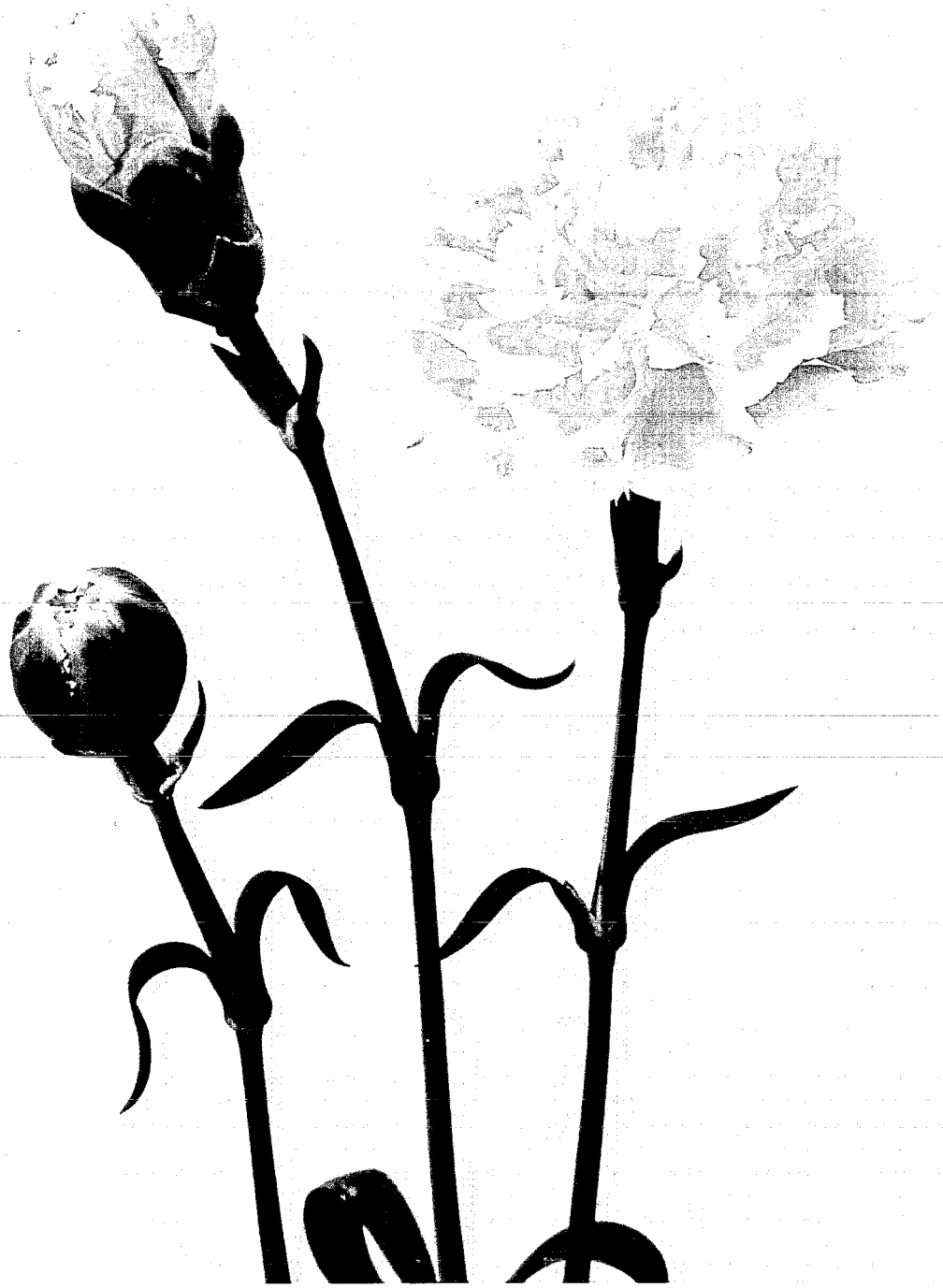

UNITED STATES PATENT AND TRADEMARK OFFICE

CERTIFICATE OF CORRECTION

PATENT NO. : Plant 7,747

DATED : December 10, 1991

INVENTOR(S) : Walter H. Jessel, Jr.

It is certified that error appears in the above-identified patent and that said Letters Patent is hereby corrected as shown below:

Column 1, line 10, change "coloration" to --carnation --.

Signed and Sealed this

First Day of June, 1993

*Attest:*

Michael K. Kirk

MICHAEL K. KIRK

*Attesting Officer*

*Acting Commissioner of Patents and Trademarks*